| United States Patent [19] | [11] Patent Number: 4,681,894 |
| Murray et al. | [45] Date of Patent: Jul. 21, 1987 |

[54] HYDROXAMIC ACIDS AND ESTERS

[75] Inventors: William V. Murray, Belle Mead; Michael P. Wachter, Bloomsbury, both of N.J.

[73] Assignee: Ortho Pharmaceutical Corporation, Raritan, N.J.

[21] Appl. No.: 912,901

[22] Filed: Sep. 26, 1986

[51] Int. Cl.[4] .................... C07C 83/10; A61K 31/085; A61K 31/185; A61K 31/21
[52] U.S. Cl. ............................ 514/507; 260/500.5 H; 514/575; 560/312
[58] Field of Search ................ 210/500.5 H; 514/575, 514/507; 560/312

[56] References Cited

U.S. PATENT DOCUMENTS

| 4,218,478 | 8/1980 | Omura et al. ................. 260/500.5 H |
| 4,604,407 | 8/1986 | Haslanger et al. ................... 514/575 |
| 4,605,669 | 8/1986 | Summers ....................... 260/500.5 H |
| 4,607,053 | 8/1986 | Karanewsky et al. ...... 260/500.5 H |
| 4,608,390 | 8/1986 | Summers ..................... 260/500.5 H |
| 4,623,661 | 11/1986 | Summers ............................. 514/575 |

FOREIGN PATENT DOCUMENTS

| 0140836 | 4/1980 | Fed. Rep. of Germany ...... 424/324 |
| 0141253 | 4/1980 | Fed. Rep. of Germany ...... 514/575 |

*Primary Examiner*—J. E. Evans
*Attorney, Agent, or Firm*—Benjamin F. Lambert

[57] ABSTRACT

The synthesis of amido substituted naphthalenes and their intermediates is described. The intermediates and amido substituted naphthalenes are useful as anti-inflammatory agents.

14 Claims, No Drawings

HYDROXAMIC ACIDS AND ESTERS

BACKGROUND OF THE INVENTION

1. Field of the Invention

The present invention relates to amido substituted naphthalenes of general formula I:

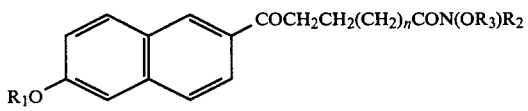

or their intermediates of general formula II:

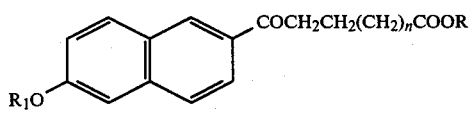

as described further below, and to a method for synthesizing the naphthalene derivatives. The amido substituted naphthalenes are pharmacologically active in alleviating inflammation, asthma, hypersensitivity, myocardial ischemia, dermatological conditions such as psoriasis, and dermatitis and gastrointestinal inflammatory conditions such as inflammatory bowel syndromes.

2. Description of the Prior Art

Nonosteroidal anti-inflammatory drugs (NSAIDs) such as indomethacin, naproxen, ibuprofen, tolectin, fenoprofen and the like have generally been shown to attenuate the biosynthesis of prostaglandins by inhibiting the activity of the enzyme cyclooxygenase. The prostaglandin end-products of the cyclooxygenase pathway are responsible for many of the early signs of inflammation including peralgesia, increases in vascular permeability leading to edema, and pyrexia. The activity and potency of the NSAIDs in reducing these signs and symptoms is, for the most part, correlated with their ability to inhibit prostaglandin biosynthesis.

The other major pathway of arachidonic acid metabolism is the lipoxygenase pathway. Lipoxygenase products of arachidonate metabolism, the leukotrienes, hydroxyeicosatetraenoic acids (HETEs) and hydroperoxyeicosatetraenoic acids, have been shown or implicated to be involved in disease states including acute and chronic inflammation, arthritis, allergic and other hypersensitivity disorders, dermatological diseases such as psoriasis, acne, atopic dermatitis, contact sensitivity, eczema and others, cardiovascular disorders secondary to myocardial ischemia such as infarction, thromboembolism or vasculities, or platelet aggregation, and hyperalgesic disorders, gynecological disorders such as dysmenorrhea, ocular inflammation, and gastrointestinal disorders such as inflammatory bowel diseases.

Leukotriene B$_4$, another product of the lipoxygenase pathway, as well as the hydroxyeicosatetraenoic acids and hydroperoxyeicosatetraenoic acids, can mediate induction of other phlogistic substances such as thromboxanes and prostacyclin, is chemotactic to inflammatory cells, and is hyperalgesic. Many of these mediators have been identified in skin, lungs, coronary circulation, eyes and other organs and in the synovial fluid of rheumatoid arthritic patients. In chronic inflammatory conditions such as rheumatoid arthritis, it is believed to be the chronic influx of leukocytes, probably mediated by leukotriene B$_4$, that is the eventual cause of joint erosion.

It is believed that inhibitors of the lipoxygenase pathway could lead to a relatively permanent effect on inflammatory disorders such as rheumatoid arthritis since they could modulate the actual mechanism of tissue and joint breakdown. Similarly, drugs that could inhibit prostaglandin synthesis via the cyclooxygenase pathway could modulate and reduce early manifestations of inflammation. Pharmacologically active compounds that can inhibit both enzyme pathways at similar concentrations (dual inhibitors) provide a more complete relief for patients suffering from arthritis, hypersensitivity, dermatological, cardiovascular, ocular, and gynecological disorders than present drugs that inhibit one pathway but not the other, as is the case for usually used NSAIDs that are predominantly inhibitors of the cyclooxygenase (prostaglandin synthesis) pathway.

Several naphthalene derivatives have been previously described. For example, naproxen, 6-methoxy-α-methyl-2-naphthalene acetic acid has been described as a potent anti-inflammatory agent which acts by a cyclooxygenase mechanism. *J. Med. Chem.* 13, 203 (1970) and *Biochem. Biophys. Res. Comm.* 46, 552 (1972). Naproxen is described in U.S. Pat. No. 4,637,767.

Nabumetone (BRL-14777), 4-(6-methoxy-2-naphthalenyl)-2-butanone with its analogs have been reported as anti-inflammatory agents with greatly reduced gastrointestinal complications. *J. Med. Chem.* 21, 1260 (1978) and *Drugs of the Future* VI, p. 35 (1981). Nabumetone is described in British Pat. No. 1,474,377.

In addition, several oxoalkanoic acid or ester substituted naphthalenes have been previously described. For example, 4-(6-methoxy-2-naphthyl)-4-oxobutyric acid and its esters have been described as intermediates for the synthesis of other compounds in *Beilstein* 10, 3rd Suppl., pp. 4414–5; *Chimia* 18, 141 (1964); *Czech. Coll. Chem. Communs.* 26, 1475 (1961) and *J. Org. Chem.* 25, 1856 (1960).

6-(6-methoxy-2-naphthyl)-6-oxohexanoic acid was prepared in *Bull. Chem. Socl. Fr.*, 1959, pp. 1943–6, by the action of acid chlorides on tetrahydropyranyl esters of HO$_2$CCH$_2$CH$_2$(CH$_2$)$_2$CO$_2$H. This reaction had not been previously reported, and circumvented the use of acid chlorides of dibasic acids in a Friedel-Crafts type acylation. 5-(6-methoxy-2-naphthyl)-5-oxopentanoic acid was prepared in a similar manner as reported in *Croat. Chem. Acta* 41, 251 (1969).

None of the prior art directed to the oxoalkanoic acid or ester substituted naphthalenes describes any biological activity for the compounds. None of this prior art describes amido substituted naphthalene compounds.

SUMMARY OF THE INVENTION

The present invention is directed to amido substituted naphthalene compounds of the formula:

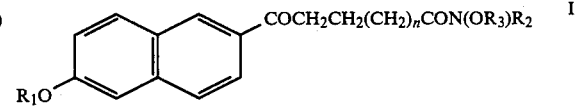

where:

R$_1$ may be C$_{1-12}$ alkyl, C$_{3-12}$ branched-chain alkyl, C$_{2-6}$ alkenyl, C$_{3-6}$ alkynyl, or an aralkyl wherein the alkyl group is C$_{1-3}$ unsubstituted or substituted with $C_{1-2}$ alkyl or hydroxyalkyl, wherein the alkyl group is $C_{1-6}$;

$R_2$ may be H, $C_{1-10}$ alkyl, $C_{3-10}$ branched-chain alkyl, $C_{5-7}$ cycloalkyl, phenyl or phenyl substituted by $C_{1-3}$ alkyl or $C_{1-3}$ alkoxy;

$R_3$ may be H or $C_{1-3}$ alkyl; and $(CH_2)_n$ may be a straight- or branched-alkyl chain of 0-5 carbons.

The present invention is further directed to intermediates of the compounds of formula I having the formula:

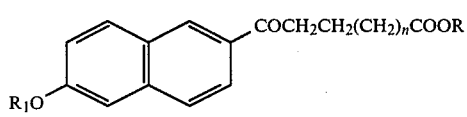

where $R_1$ and $(CH_2)_n$ are as defined above. $R_1$ may also be H and $R_4$ may be H or $C_{1-3}$ alkyl with the proviso that when $(CH_2)_n$ is an alkyl chain of 0-2 carbons, $R_1$ is not $C_{1-2}$ alkyl.

The compounds of formula I or II are useful as anti-inflammatory agents. The compounds inhibit the cyclooxygenase pathway and may additionally inhibit the lipoxygenase pathway.

DETAILED DESCRIPTION OF THE INVENTION

The invention in its broadest aspects relates to amido substituted naphthalene compounds and intermediates thereof which have an anti-inflammatory activity. The amido substituted naphthalene compounds demonstrating an anti-inflammatory activity are shown by formula I above. The intermediates of these compounds which also have an anti-inflammatory activity are shown by formula II above.

The preferred compounds are those wherein $R_1$ is $CH_3$, $R_2$ is H, $C_{1-6}$ alkyl, $C_{3-4}$ branched-chain alkyl, cyclohexyl and phenyl, and $R_3$ is H or $CH_3$. The most preferred compounds are those wherein $R_1$ is $CH_3$, $R_2$ is $CH_3$, $CH(CH_3)_2$ or phenyl, $R_3$ is H, and $(CH_2)_n$ is a straight-alkyl chain of 2 carbons, or $R_1$ is $CH_3$, $R_2$ is $CH_3$, $R_3$ is $CH_3$ and $(CH_2)_n$ is a straight-alkyl chain of 2 carbons.

The compounds of formulas I and II can be prepared as shown in the following schemes:

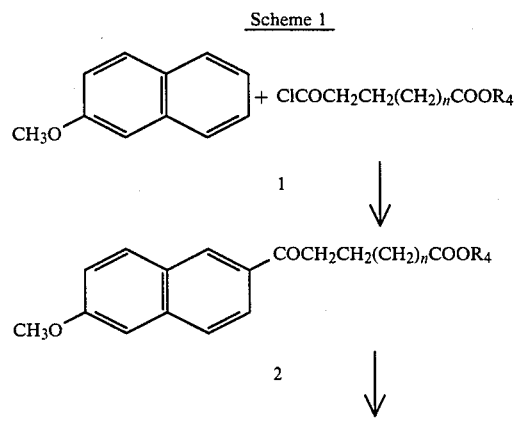

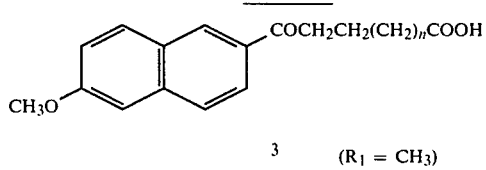

The compounds of formula II are prepared as follows: A compound of the formula $ClCOCH_2CH_2(CH_2)_nCOOR_4$ is mixed with $AlCl_3$ in an inert solvent such as methylene chloride, and then 2-methoxy-naphthalene 1 is added. The reaction is allowed to proceed at room temperature for about 1-4 hours to produce the oxoalkanoate ester 2. The ester 2 is then converted to the acid 3 by dissolving the ester 2 in an aqueous alcoholic solvent and treating with an alkali metal base at reflux temperatures for about 2-6 hours. Suitable alcohols include methanol and ethanol. Preferred bases are potassium hydroxide and sodium hydroxide. Alternatively, the ester 2 or acid 3 can be prepared by any of the prior art methods described above.

The oxoalkanoic acid or esters in which $R_1$ is other than $CH_3$ are prepared by dissolving the oxoalkanoic acid 3 where R$_1$ is CH$_3$ in a polar solvent, such as dimethylformamide, and slowly adding the solution to a solution of sodium hydride and butanethiol (to generate butylsulfide in situ) in a polar solvent such as dimethylformamide at reflux temperatures. The mixture is heated at reflux for about 1-4 hours to produce the acid 4. The acid 4 is esterified by dissolving it in an alcoholic solvent and treating with HCl at reflux temperatures to produce the ester 5. Suitable alcohols include ethanol and methanol. The ester 5 is then reacted with a compound of the formula R$_1$X, wherein X is a halogen atom such as bromo, chloro or iodo and R$_1$ is as defined in formula I, in a solvent such as acetone at reflux temperatures for about 2-56 hours to produce the ester 2. The ester 2 is converted to the acid 3 as previously described.

The compounds of formula I are prepared as follows: The oxoalkanoic acid 3 is dissolved in a solvent such as benzene and oxalyl chloride is added. The mixture is reacted at reflux for about 1-3 hours to produce the acid chloride. The acid chloride is dissolved in an inert solvent such as tetrahydrofuran and added dropwise to an aqueous solvent, such as tetrahydrofuran:H$_2$O (2:1) containing a compound of the formula HNR$_2$OR$_3$ and a base such as triethyl amine at 0° C. The reaction proceeds at 0° C. for about 0.5-1.0 hour and then at room temperature for about 2-12 hours to produce the amido substituted naphthalene compounds of formula I.

Pharmaceutical compositions containing a compound of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit. e.g., tablet, capsule, powder, injection, teaspoonful and the like, from about 0.01 to about 500 mg/kg, and preferably from about 0.1 to about 50 mg/kg of the active ingredient.

The following examples describe the invention in greater particularity and are intended to be a way of illustrating but not limiting the invention.

Melting points (mp) were determined on a Thomas-Hoover apparatus, and are uncorrected. The infrared (IR) spectra were recorded on a Beckman Instruments IR-B spectrophotometer and are expressed in reciprocal centimeters. Nuclear magnetic resonance (NMR) spectra for hydrogen atoms were measured in the indicated solvent with tetramethylsilane (TMS) as the internal standard on a Varian T-60A or an IBM WP-100 spectrometer. The values are expressed in parts per million down-field from TMS. Parenthesized, underlined hydrogens were assigned to the resonance positions immediately before the parentheses. EI and CI mass spectra were obtained on a Finnigan 1015D quadrupole mass spectrometer coupled to a Finnigan 9500 gas chromatograph or a Finnigan MAT 8230 Double Focusing high resolution mass spectrometer.

EXAMPLE 1

Ethyl 8-(6-methoxy-2-naphthyl)-8-oxooctanoate

To a slurry of AlCl$_3$ (26.7 g, 200 mM) in CH$_2$Cl$_2$ (300 ml) was added ethyl suberyl chloride (22.03 g, 100 mM). After 15 minutes, a solution of 2-methoxy-naphthalene (15.82 g, 100 mM) in CH$_2$Cl$_2$ (100 ml) was added to the above slurry and stirring of the reaction mixture was continued for 2 hours at room temperature. The reaction was quenched with 300 ml concentrated HCl in 300 g ice and the resulting layers separated. The aqueous layer was washed with CH$_2$Cl$_2$ and the combined CH$_2$Cl$_2$ layer was washed with 5% NaHCO$_3$ (200 ml). The CH$_2$Cl$_2$ layer was filtered, dried (Na$_2$SO$_4$), and concentrated in vacuo to give a residue which was purified via flash chromatography on silica using CHCl$_3$ as eluent followed by a similar column with hexane:EtOAc (3:2) as eluent. The desired product was further purified by recrystallization (Et$_2$O/Hexane) to give the title compound as a white solid (5.3 g, 15% yield), mp=77°-78° C. NMR (CDCl$_3$) 1.2 (t, 3H, CH$_2$C$\underline{H}_3$), 1.4-1.9 (m, 8H, 4×CH$_2$), 2.3 (m, 2H), 3.0 (m, 2H), 3.9 (s, 3H, OC$\underline{H}_3$), 4.1 (q, 2$\underline{H}$, OC$\underline{H}_2$CH$_3$), 7.0-8.4 (m, 6H, aromatic $\underline{H}$); IR (KBr) 1740, 1670; MS, m/e 342 (M+).

Theor. C$_{21}$H$_{26}$O$_4$: C, 73.66; H, 7.65; Found: C, 73.80; H, 7.63

EXAMPLES 2-4

Following the procedure of Example 1 but substituting ethyl adipyl chloride, methyl azelayl chloride or methyl suberyl chloride for the ethyl suberyl chloride, the following compounds were prepared.

(2) Ethyl 6-(6-methoxy-2-naphthyl)-6-oxohexanoate

White solid, mp=64°-65° C.; MS, m/e 314 (M+)

Theor. C$_{19}$H$_{22}$O$_4$: C, 72.59; H, 7.05; Found: C, 72.80; H, 7.30

(3) Methyl 9-(6-methoxy-2-naphthyl)-9-oxononanoate

White solid, mp=74°-76° C.; MS, m/e 342 (M+)

Theor. C$_{21}$H$_{26}$O$_4$: C, 73.66; H, 7.65; Found: C, 73.30; H, 7.67

(4) Methyl 8-(6-methoxy-2-naphthyl)-8-oxooctanoate

White solid, mp=95°-96° C.; MS, m/e 328 (M+)

Theor. C$_{20}$H$_{24}$O$_4$: C, 73.15; H, 7.37; Found: C, 73.03; H, 7.70

EXAMPLE 5

Following the procedure of the cited reference, the following compound was prepared.

(5) 6-(6-Methoxy-2-naphthyl)-6-oxohexanoic acid

*Bull. Soc. Chim. Fr.*, 1959, pp. 1943-6

EXAMPLE 6

8-(6-Methoxy-2-naphthyl)-8-oxooctanoic acid

The compound from Example 4 (1.5 g, 4.6 mM) was hydrolyzed with ethanolic KOH at reflux to give the title compound as a white solid (1.0 g, 73% yield) after recrystallization from EtOAc, mp=148°-149° C.; MS, m/e 314 (M+).

Theor. $C_{19}H_{22}O_4$: C, 72.59; H, 7.05; Found: C, 72.74; H, 7.25

Similarly, the compound from Example 3 is hydrolyzed to yield 9-(6-methoxy-2-naphthyl)-9-oxononanoic acid.

EXAMPLE 7

6-(6-Hydroxy-2-naphthyl)-6-oxohexanoic acid

Butyl sulfide was generated by placing NaH (2.57 g, 0.11 mol) in a 500 ml round bottom flask, adding butanethiol (5.14 ml, 0.48 mol) and stirring for 5 minutes. DMF (200 mls) was added and the reaction heated at reflux. Slowly, 6-(6-methoxy-2-naphthyl)-6-oxo-hexanoic acid (Example 5) (7.2 g, 0.25 mol) in DMF (100 ml) was added to the reaction and heated at reflux for 1 hour. The methyl butyl sulfide and DMF were vacuum distilled (7 torr, 28° C.) to leave a bright yellow powder that was dissolved in water and precipitated with 5% HCl. The precipitate was filtered, dissolved in ethyl acetate (1800 ml), dried ($Na_2SO_4$), filtered and evaporated to give a yellow solid that was recrystallized (ethyl acetate) to give the title compound (5.38 grams, 79% yield), mp 191-193° C.; MS, m/e 272 (M+).

Theor. $C_{16}H_{16}O_4$: C, 70.57; H, 5.92; Found: C, 70.21; H, 5.90

The 6-hydroxynaphthalene compounds of the acids produced in Example 6 are prepared by following the above procedure using the acids prepared in Example 6.

EXAMPLE 8

Ethyl 6-(6-hydroxy-2-naphthyl)-6-oxohexanoate

The hexanoic acid produced in Example 7 (3.0 g, 9.2 mM) was esterified with EtOH/HCl (200 ml) at reflux to give after recrystallization (EtOH) the title compound as a white solid (2.72 g, 82% yield), mp 139°-142° C.; MS, m/e 300 (M+).

Theor. $C_{18}H_{20}O_4$: C, 71.98; H, 6.71; Found: C, 72.40; H, 6.93

The additional 6-hydroxynaphthalene oxoalkanoic acids produced in Example 7 are esterified in accordance with the above procedure.

EXAMPLE 9

Ethyl 6-[6-(3-methylbutyloxy)-2-naphthyl]-6-oxohexanoate

The hexanoic acid ester produced in Example 8 (2 g, 6.7 mM), $K_2CO_3$ (0.94 g, 6.8 mM) and 1-bromo-3-methylbutane (0.82 ml, 6.8 mM) in acetone (100 ml) were heated at reflux for 56 hours. The cooled reaction mixture was filtered, concentrated in vacuo and the residue purified via flash chromatography on silica (25% EtOAc/Hexane). Recrystallization ($Et_2O$) gave the title compound as a white solid (1.2 g, 45% yield), mp 65°-66° C., NMR ($CDCl_3$) 1.0-1.5 (m, 9H, 3-$CH_3$), 1.6-2.0 (m, 7H), 2.4 (m, 2H), 3.2 (m, 2H), 4.0-4.4 (m, 4H), 7.0-8.2 (m, 6H, aromatic H); IR (KBr) 1740, 1680; MS, m/e 370 (M+).

Theor. $C_{23}H_{30}O_4$: C, 74.56; H, 8.16; Found: C, 74.44; H, 8.09

EXAMPLES 10-14

Following the procedure of Example 9 but substituting 2-bromoethanol, benzyl bromide, allyl bromide, 2-bromopentane and propargyl bromide for the 1-bromo-3-methyl-butane, the following compounds were prepared.

(10) Ethyl 6-[6-(2-hydroxyethoxy)-2-naphthyl-6-oxohexanoate

Yellow solid, mp=83°-84° C.; MS, m/e 344 (M+)

Theor. $C_{20}H_{24}O_5$: C, 69.75; H, 7.02; Found: C, 69.53; H, 7.24

(11) Ethyl 6-(6-benzyloxy-2-naphthyl)-6-oxohexanoate

White solid, mp=97°-98° C.; MS, m/e 390 (M+)

Theor. $C_{25}H_{26}O_4$: C, 76.90; H, 6.71; Found: C, 76.72; H, 6.98

(12) Ethyl 6-(6-allyloxy-2-naphthyl)-6-oxohexanoate

White solid, mp=82°-84° C.; MS, m/e 340 (M+)

Theor. $C_{21}H_{24}O_4$: C, 74.09; H, 7.11; Found: C, 73.90; H, 7.25

(13) Ethyl 6-(6-(1-methylbutyloxy)-2-naphthyl-6-oxohexanoate

White solid, mp=48°-49° C.; MS, m/e 370 (M+)

Theor. $C_{23}H_{30}O_4$: C, 74.56; H, 8.16; Found: C, 74.34; H, 8.51

(14) Ethyl 6-(6-propynyloxy-2-naphthyl)-6-oxohexanoate

White solid, mp=100°-101° C.; MS, m/e 338 (M+)

Theor. $C_{21}H_{22}O_4$: C, 74.53; H, 6.55; Found: C, 74.70; H, 6.82

When in the procedures of Examples 9-14, the 6-hydroxynaphthalene oxoalkanoic acid esters produced in Example 8 are employed, the corresponding -8-oxooctanoate and -9-oxononanoate derivatives are prepared.

When in the above procedures, vinyl bromide, 6-bromo-1-hexene, bromoethane, 1-bromo-3-phenylpropane, 2-bromo-3-phenylpropane, and 3-methylbenzyl bromide are employed, the corresponding 6-vinyloxy-2-naphthyl, 6-(1-hexen-6-yl)oxy-2-naphthyl, 6-ethoxy-2-naphthyl, 6-(3-phenylpropyloxy)-2-naphthyl, 6-(1-methyl-2-phenylethoxy)-2-naphthyl and 6-(3-methylbenzyloxy)-2-naphthyl derivatives are prepared. The oxoalkanoic acids are prepared by following the procedure described in Example 6.

EXAMPLE 15

N-Hydroxy-N-methyl-6-(6-methoxy-2-naphthyl)-6-oxohexanamide

The compound prepared in Example 5 (1.43 g, 5.0 mM) was dissolved in dry benzene (50 ml). Oxalyl chloride (0.75 g, 6 mM) was added and the solution refluxed for 2 hours, cooled, and concentrated in vacuo to give the acid chloride as a yellow solid. The acid chloride was then dissolved in THF (30 ml), and added dropwise to a solution of N-methyl hydroxylamine.HCl (0.42 g, 5 mM) and $Et_3N$ (3 ml) in THF:$H_2O$ (2:1, 30 ml) at 0° C. The resulting solution was stirred for 1 hour at 0° C. and then for 1 hour at room temperature. The reaction mixture was transferred to a separatory funnel containing 100 ml of Et$_2$O and the organic layer was separated and washed with 5% HCl (15 ml, 2×) and brine (15 ml, 2x), dried (Na$_2$SO$_4$), filtered and concentrated in vacuo. Recrystallization (Et$_2$O) gave the title compound as a white solid (900 mg, 57% yield), mp=116°-118° C. NMR (CDCl$_3$) 1.7-2.0 (m, 4H, —CH$_2$—CH$_2$—), 2.2-2.6 (m, 2H), 3.1 (t, J=7 Hz, 2H), 3.3 (s, 3H, N—CH$_3$), 3.95 (3, 3H, OCH$_3$), 7.1-8.4 (m, 6H, aromatic H); IR (KBr) 3150, 1785, 1630; MS m/e 315 (M+).

Theor. C$_{18}$H$_{21}$NO$_4$: C, 68.55; H, 6.71; N, 4.44; Found: C, 68.26; H, 6.44; N, 4.24

EXAMPLES 16-24

Following the procedure of Example 15 but substituting the corresponding amine.HCl for the N-methylhydroxylamine.HCl, the following compounds were prepared.

(16)
N-Hydroxy-6-(6-methoxy-2-naphthyl)-6-oxohexanamide

White solid, mp=139°-142° C.; MS, m/e 301 (M+)

(17)
N-Ethyl-N-hydroxy-6-(6-methoxy-2-naphthyl)-6-oxohexanamide

White solid, mp=100°-101° C.; MS, m/e 329 (M+)
Theor. C$_{19}$H$_{23}$NO$_4$: C, 69.28; H, 7.04; N, 4.25; Found: C, 69.18; H, 7.28; N, 4.25

(18)
N-Butyl-N-hydroxy-6-(6-methoxy-2-naphthyl)-6-oxohexanamide

White solid, mp=112°-113° C.; MS, m/e 357 (M+)
Theor. C$_{21}$H$_{27}$NO$_4$: C, 70.56; H, 7.61; N, 3.92; Found: C, 70.50; H, 7.77; N, 3.91

(19)
N-Heptyl-N-hydroxy-6-(6-methoxy-2-naphthyl)-6-oxohexanamide

White solid, mp=119°-120° C.; MS, m/e 399 (M+)
Theor. C$_{24}$H$_{33}$NO$_4$: C, 72.15; H, 8.33; N, 3.51; Found: C, 72.09; H, 8.55; N, 3.51

(20)
N-tert-Butyl-N-hydroxy-6-(6-methoxy-2-naphthyl)-6-oxohexanamide

White solid, mp=85°-87° C.; MS, m/e 357 (M+)
Theor. C$_{21}$H$_{27}$NO$_4$: C, 70.56; H, 7.61; N, 3.92; Found: C, 70.58; H, 7.69; N, 3.86

(21)
N-Hydroxy-N-cyclohexyl-6-(6-methoxy-2-naphthyl)-6-oxohexanamide

Yellow solid, mp=133°-135° C.; MS, m/e 383 (M+)
Theor. C$_{23}$H$_{29}$NO$_4$: C, 72.04; H, 7.62; N, 3.64; Found: C, 71.88; H, 7.84; N, 3.59

(22)
N-Hydroxy-N-phenyl-6-(6-methoxy-2-naphthyl)-6-oxohexanamide

Yellow solid, mp=153°-154° C.; MS, m/e 377 (M+)
Theor. C$_{23}$H$_{23}$NO$_4$: C, 73.19; H, 6.14; N, 3.71; Found: C, 72.80; H, 6.41; N, 3.74

(23)
N-Methoxy-N-methyl-6-(6-methoxy-2-naphthyl)-6-oxohexanamide

White solid, mp=97°-98° C.; MS, m/e 329 (M+)
Theor. C$_{19}$H$_{23}$NO$_4$: C, 69.28; H, 7.04; N, 4.25; Found: C, 69.14; H, 7.18; N, 4.08

(24)
N-Hydroxy-N-isopropyl-6-(6-methoxy-2-naphthyl)-6-oxohexanamide

White solid, mp=123°-124° C.; MS, m/e 343 (M+)
Theor. C$_{20}$H$_{25}$NO$_4$: C, 69.95; H, 7.34; N, 4.08; Found: C, 69.53; H, 7.48; N, 3.99

When in the procedures of Examples 15-24, the oxoalkanoic acids prepared as described in Examples 9-14 are substituted for the oxohexanoic acid of Examples 15-24, the corresponding oxoalkanamides are obtained.

EXAMPLE 25

In Vivo Alleviation of Inflammation

Polyarthritis was induced in Lewis strain laboratory rats (weight=about 200 grams) by injection of a suspension of *Mycobacterium butyricum* in mineral oil into the subplantar tissue of the mammals' hind paws. On day 10 after the injection, the rats were assigned to groups, and paw volumes and body weights were recorded. Paw volumes of the contralateral, uninjected hind paw were determined by mercury plethylsmography. Per os (p.o.) dosing began and continued for five consecutive days thereafter. On day 14 after the initial injection, approximately four hours after the final dose was administered, paw volumes and body weights were recorded and quantitated.

Anti-inflammatory activity of the substituted naphthalene compounds is expressed as the present inhibition of paw volume increase. The results of this study for several compounds are shown in Table I.

TABLE 1

| Anti-Inflammatory Effect of Representative Substituted Naphthalene Derivatives | | |
| --- | --- | --- |
| Compound (Example) | Dose (mg/kg) | % Inhibition Oral Dosage* |
| 1 | 50 | 48 |
| 2 | 22 | 50 |
| 4 | 50 | 53 |
| 6 | 50 | 47 |
| 8 | 50 | 12 |
| 12 | 50 | 44 |
| 14 | 50 | 23 |
| 15 | 40 | 34 |
| 17 | 50 | 23 |
| 21 | 50 | 33 |
| 22 | 50 | 28 |
| 23 | 50 | 60 |
| 24 | 50 | 51 |

*Percentage inhibition of pad swelling from oral dosages in the amount of the compound shown.

EXAMPLE 26

In Vivo Inhibition of 5-lipoxygenase

The compounds of the invention may be used as pharmaceutical agents in the treatment of inflammation and/or allergic reactions. Such activity can be exhibited by reference to the ability of the compound to inhibit the action of the enzyme 5-lipoxygenase in vitro, and the testing was carried out by the following procedure.

Preparation of Cells and Cell-Free Homogenates.

Rat basophilic leukemia cells (RBL-1) were grown in Eagle's Minimal Essential Medium containing 10% fetal calf serum. 5% calf serum, 1% glutamine and 50 mg/l gentamycin were maintained at 37° C. in an atmosphere containing 5% $CO_2$. Exponentially growing cells were harvested by centrifugation at 400×g for 10 minutes at 4° C. and were washed once with Dulbecco's phosphate buffered saline containing 0.87 mM $CaCl_2$. The cells were resuspended in the same buffer at a concentration of $1.85 \times 10^7$ cells/ml.

5-HETE Production in Whole Cells.

RBL-1 cells ($1.57 \times 10^7$ cells/tube) were preincubated for 10 minutes at 37° C. in the presence of the indicated drugs or vehicle (1% DMSO). Following the transfer of the assay tubes to an icebath, the reaction was initiated by the sequential addition of calcium ionophore A23187, an agent which increases the ability of divalent ions such as $Ca^{++}$ to cross biological membranes (final concentration=1.9 μM) and 55 μM 1-$^{14}C$-arachidonic acid (New England Nuclear) at a final specific activity of 3000-4000 cpm/nmole. The final volume in each tube was 1 ml. The assay tubes were incubated at 37° C. for 5 minutes, and the reaction was stopped by transferring the tubes to ice and adjusting the pH of the reaction mixture to pH 3.0-3.5 by the addition of 1M citric acid.

Isolation and Quantiation of 5-HETE.

In order to isolate the $\Delta_5$-lipoxygenase product, $^{14}C$-5-HETE that was formed from arachidonic acid, each assay tube was extracted once with 6 volumes of anhydrous diethyl ether. In most assays, the recovery of product was estimated by determining the total amount of radioactivity recovered after extraction. In the remaining assays the recovery of $^{14}C$-5-HETE was monitored by addition of trace quantities of $^3H$-5-HETE (New England Nuclear) prior to extraction. The ether fractions from each sample were dried under nitrogen, redissolved and spotted on Gleman silica gel-impregnated glass fiber sheets. The plates were developed in iso-octane:2-butanone:glacial acetic acid (100:9:1). The area of each plate corresponding to added 5-HETE standard was visualized in an iodine chamber. The amount of $^{14}C$-5-HETE presented was quantitated by liquid scintillation counting in Aquasol II (New England Nuclear) and corrected for recovery. The percent inhibition of lipoxygenase activity represents the decrease in the amount of product formed from arachidonic acid by the cells or cell supernatant in the presence of drug. The values for negative controls (assays incubated on ice in the presence of citric acid) were always less than 10% of the positive controls and were subtracted from each tube. The $IC_{50}$ is the concentration of drug which is required for 50% inhibition of the enzyme, as determined graphically from assays using multiple concentrations of drug. For drugs which did not inhibit the enzyme by 50% at the highest concentration tested (10 μM), their activity is reported as having an $IC_{50}$ which is greater than 10 μM. The results are shown in Table II.

TABLE II

| Lipoxygenase Inhibitory Activity | |
|---|---|
| Compound (Example) | $IC_{50}$* (μM) |
| 2 | >10 |
| 8 | >10 |
| 12 | >10 |
| 15 | 0.25 |
| 16 | 10 |
| 17 | 0.11 |

TABLE II-continued

| Lipoxygenase Inhibitory Activity | |
|---|---|
| Compound (Example) | $IC_{50}$* (μM) |
| 18 | 0.37 |
| 19 | 1.6 |
| 20 | 0.45 |
| 21 | 0.4 |
| 22 | 0.1 |
| 23 | >10 |
| 24 | 0.12 |

*In vitro concentration required for compound to inhibit RBL cell lipoxygenase activity by 50%.

What is claimed is:

1. A compound of the formula

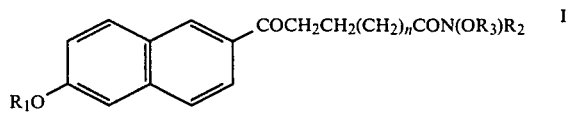

where
$R_1$ is $C_{1-12}$ alkyl, $C_{3-12}$ branched-chain alkyl, $C_{2-6}$ alkenyl, $C_{3-6}$ alkynyl or aralkyl wherein the alkyl group of the aralkyl is a $C_{1-3}$ alkyl and wherein the aralkyl group is unsubstituted or substituted with a $C_{1-2}$ alkyl or hydroxyalkyl wherein the alkyl group is $C_{1-6}$;
$R_2$ is H, $C_{1-10}$ alkyl, $C_{3-10}$ branched-chain alkyl, $C_{5-7}$ cycloalkyl, phenyl or phenyl substituted with $C_{1-3}$ alkyl or $C_{1-3}$ alkoxy;
$R_3$ is H or $C_{1-3}$ alkyl; and
$(CH_2)_n$ is a straight- or branched-alkyl chain wherein n is 0-5.

2. A compound of claim 1 wherein $R_1$ is $CH_3$.

3. A compound of claim 1 wherein $R_2$ is H, $C_{1-6}$ alkyl, $C_{3-4}$ branched-chain alkyl, cyclohexyl or phenyl.

4. A compound of claim 1 wherein $R_3$ is H or $CH_3$.

5. A compound of claim 1 wherein $R_1$ is $CH_3$, $R_2$ is $CH(CH_3)_2$ or phenyl, $R_3$ is H and $(CH_2)_n$ is a straight-alkyl chain of 2 carbons.

6. A compound of claim 1 wherein $R_1$, $R_2$ and $R_3$ are each $CH_3$ and $(CH_2)_n$ is a straight-alkyl chain of 2 carbons.

7. A compound of claim 1 selected from the group consisting of N-hydroxy-6-(6-methoxy-2-naphthyl)-6-oxohexanamide; N-ethyl-N-hydroxy-6-(6-methoxy-2-naphthyl)-6-oxohexanamide; N-butyl-N-hydroxy-6-(6-methoxy-2-naphthyl)-6-oxohexanamide; N-heptyl-N-hydroxy-6-(6-methoxy-2-naphthyl)-6-oxohexanamide; N-tert-butyl-N-hydroxy-6-(6-methoxy-2-naphthyl)-6-oxohexanamide; and N-hydroxy-N-cyclohexyl-6-(6-methoxy-2-naphthyl)-6-oxohexanamide.

8. A compound of claim 1 selected from the group consisting of N-hydroxy-N-methyl-6-(6-methoxy-2-naphthyl)-6-oxohexanamide; N-hydroxy-N-phenyl-6-(6-methoxy-2-naphthyl)-6-oxohexanamide; N-methoxy-N-methyl-6-(6-methoxy-2-naphthyl)-6-oxohexanamide; and N-hydroxy-N-isopropyl-6-(6-methoxy-2-naphthyl)-6-oxohexanamide.

9. A pharmaceutical composition for topical, oral, parenteral and aerosol administration, comprising an effective amount of a compound according to claim 1 as the active ingredient dispersed in a pharmaceutically acceptable carrier.

10. The pharmaceutical composition according to claim 9 wherein said compound is capable of inhibiting both the cyclooxygenase and lipoxygenase pathways in the amount present in the composition when said composition is introduced into a mammal.

11. A method for alleviating inflammation in a mammal exhibiting an inflammatory response comprising administering to said mammal a pharmaceutical composition according to claim 9.

12. A method for treating inflammatory conditions of the skin in a mammal, including psoriasis and dermatitis, comprising administering to said mammal a pharmaceutical composition according to claim 9.

13. A method for treating asthma and allergic hypersensitivity diseases in a mammal comprising administering to said mammal an effective amount of a pharmaceutical composition according to claim 9.

14. A method for treating cardiovascular disorders in a mammal involving products of the cyclooxygenase and/or lipoxygenase pathways comprising administering to said mammal an effective amount of a pharmaceutical composition according to claim 9.

* * * * *